United States Patent [19]

Gähwiler et al.

[11] 4,453,934
[45] Jun. 12, 1984

[54] INJECTION SYRINGE FOR THE SUCCESSIVE INJECTION OF TWO LIQUIDS INTO THE BLOOD VESSELS OF LIVING BODIES

[75] Inventors: Hermann Gähwiler; Adrian Lorenz, both of Zurich, Switzerland

[73] Assignee: Contraves AG, Zurich, Switzerland

[21] Appl. No.: 436,307

[22] Filed: Oct. 25, 1982

[30] Foreign Application Priority Data

Nov. 11, 1981 [CH] Switzerland .......................... 7253/81

[51] Int. Cl.³ .............................................. A61M 5/00
[52] U.S. Cl. ...................................... 604/191; 604/87
[58] Field of Search ........................ 604/87, 88, 89, 90, 604/91, 191

[56] References Cited

U.S. PATENT DOCUMENTS

| | | | |
|---|---|---|---|
| 1,943,120 | 1/1934 | Kabnick | 604/87 |
| 3,684,136 | 8/1972 | Baumann | 604/87 |
| 3,739,947 | 6/1973 | Baumann et al. | 604/87 |
| 3,888,239 | 6/1975 | Rubinstein . | |
| 4,306,554 | 12/1981 | Schwartz et al. | 604/87 |

FOREIGN PATENT DOCUMENTS 2194451 3/1974 France .
2251339 6/1975 France .
398446 8/1965 Switzerland .
558742 12/1974 Switzerland .

*Primary Examiner*—John D. Yasko
*Attorney, Agent, or Firm*—Werner W. Kleeman

[57] ABSTRACT

An injection syringe is disclosed which comprises a cylinder equipped at one end with an attachment flange and at the other end, near to an outlet or discharge opening thereof, with a catheter connection. A piston member is insertable into the cylinder, and a container or receptacle is located between the piston member and the outlet or discharge opening. The container is provided with reference fracture locations and is freely displaceable within the cylinder in the lengthwise direction thereof. This container is filled with one of two liquids. After the ejection of the other liquid located within the cylinder externally of the container the container splits open and releases the injection the liquid contained therein. The injection syringe can be used, for instance, for the injection of a contrast agent followed by flushing with a physiological saline or salt solution, but also can be used in all other fields of application where it is desired to apply in timewise succession two liquids.

17 Claims, 5 Drawing Figures

INJECTION SYRINGE FOR THE SUCCESSIVE INJECTION OF TWO LIQUIDS INTO THE BLOOD VESSELS OF LIVING BODIES

CROSS-REFERENCE TO RELATED APPLICATION

This application is related to the commonly assigned, copending U.S. application Ser. No. 438,456 filed Nov. 1, 1982 entitled "Injection Apparatus For The Dosed-Delivery Of A Liquid".

BACKGROUND OF THE INVENTION

The present invention relates to a new and improved construction of an injection syringe, also simply referred to as a syringe, for the successive injection of two liquids into the blood vessels of living bodies or the like.

In its more particular aspects, the syringe for the successive injection of two liquids, especially although not exclusively, a liquid contrast agent and a flushing or rinsing liquid, into the blood vessels of living bodies, is of the type comprising a cylinder which is provided at one side or end thereof with an attachment or connection flange and at the other side or end thereof contains, at the region of an outlet or discharge opening, a catheter connection or equivalent structure. A piston member can be inserted into the cylinder.

Particularly in the field of computer tomography there has gained increasing importance an injection technique, wherein immediately after injecting a contrast agent there is injected a physiological saline or salt solution. However, with the state-of-the-art syringes, for instance as disclosed in Swiss Pat. No. 580,427, there only can be injected during one working operation a single liquid. Thus, there must be employed in each case two syringes, each of which is filled with a respective liquid and each of which is provided with a respective drive. Apart from the high costs involved with the employment of two syringes and two drives the use of two systems requires a correspondingly greater expenditure in terms of servicing and operating the same as well as monitoring such systems.

SUMMARY OF THE INVENTION

Therefore, with the foregoing in mind it is a primary object of the present invention to provide an improved construction of syringe for the successive injection of two liquids in a manner which is not afflicted with the aforementioned drawbacks and limitations of the prior art proposals.

Another and more specific object of the present invention aims at the provision of a new and improved construction of a syringe of the aforementioned type, by means of which it is possible to effectively inject in succession two liquids, and wherein there are effectively complied with the high requirements as concerns reliability and accuracy which are placed upon such medical equipment.

Still a further significant object of the present invention is directed to a new and improved construction of a syringe for the successive injection of two liquids, which syringe is relatively simple in construction and design, quite economical to manufacture, extremely easy to use, and not readily subject to breakdown or malfunction.

Now in order to implement these and still further objects of the invention, which will become more readily apparent as the description proceeds, the syringe of the present development is manifested by the features that, there is provided a container or receptacle in the interior of the cylinder between the piston member and the outlet or discharge opening. This container is essentially freely displaceable within the cylinder. The container or receptacle can be filled with one of the two liquids, especially the flushing or rinsing liquid, and is provided with reference fracture locations or reference opening locations. The container, following ejection of the other liquid contained within the cylinder, especially the liquid contrast agent, opens at the reference fracture locations or reference opening locations and releases the therein contained liquid for injection purposes.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
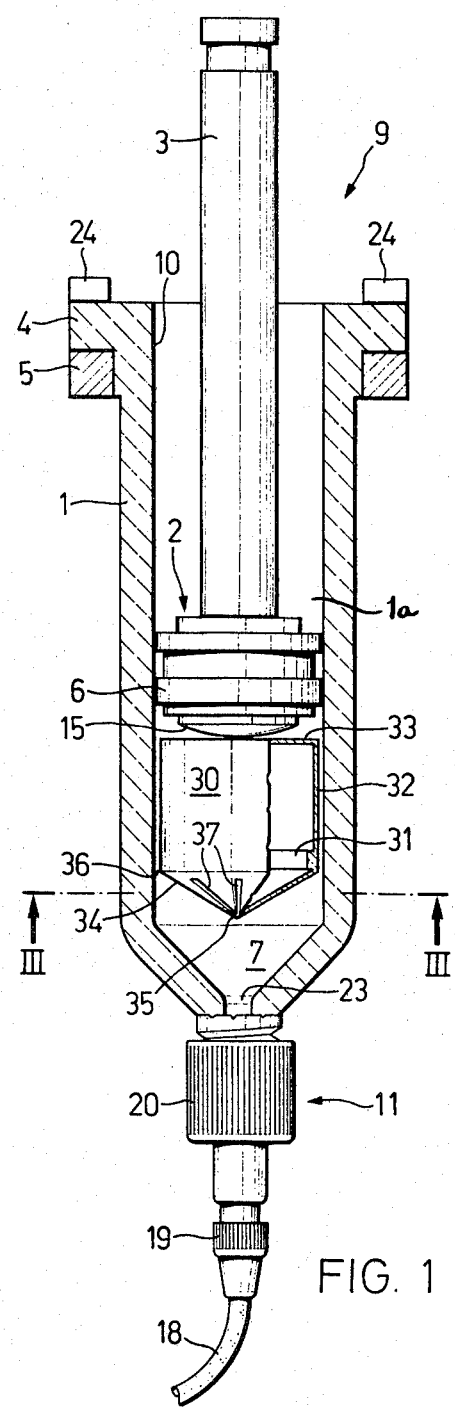
FIG. 1 schematically illustrates a syringe constructed according to the present invention, partially in longitudinal sectional view, and depicting a catheter connected therewith.

Describing now the drawings, in FIG. 1 there has been illustrated an exemplary embodiment of an injection syringe or syringe 9 which comprises a hollow cylinder 1 possessing an internal compartment 1a, a piston member or piston 2 containing a slide ring or seal 6 and a piston rod 3 operatively connected with the piston member 2 as well as a container or receptacle 30 which is displaceably mounted in the internal compartment 1a of the cylinder 1. The piston member 2 is insertable into the hollow cylinder 1 and can be moved therein in the lengthwise direction thereof. At the one side or end of the cylinder 1 there is connected a catheter 18 or equivalent structure by means of a suitable connection element 19 and a screw cap or clamping nut 20 or the like. At the other side or end of the cylinder 1 there is arranged a connection or attachment flange 4, a ring member 5 located behind the connection flange 4 and at least two clamping cams or detents 24 which render possible the connection of the syringe 9 at any suitable drive which appropriately moves the piston member 2.

Figure 2:
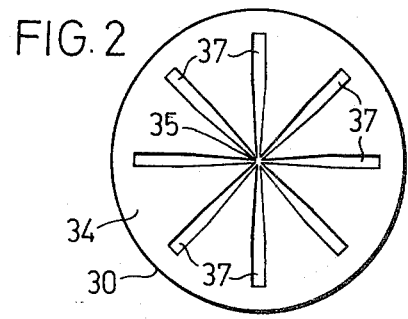
FIG. 2 is a top plan view of an end wall of a container or receptacle arranged in the syringe arrangement of FIG. 1.

The container or receptacle 30 which can be inserted into the interior of the hollow cylinder 1 contains a substantially cone-shaped end or bottom wall 34, a substantially cylindrical side wall 32 and a rear or top wall 33. This container 30 is formed, for instance, from polyethylene, but it is to be specifically understood that such container or receptacle 30 also can be fabricated from any other suitable material. As explained, the side wall 32 of the container or receptacle 30 possesses a substantially cylindrical configuration and has an outer diameter which is smaller than the inner diameter of the cylinder 1. Between the cylinder inner wall 10 and the side wall 32 of the inserted container or receptacle 30 there is present a substantially cylindrical or ring-shaped gap 36 which is wide enough in order to allow the throughflow of a suitable liquid contrast agent in the direction of the catheter 18, and which furthermore allows free displacement of the container or receptacle 30 in the lengthwise direction of the cylinder 1. The side wall 32 of the container 30 is reinforced in a ring-shaped configuration by a reinforcement ring member 31 at the region of the end wall 34. As also explained, this end wall 34 possesses a substantially conical-shaped configuration and also contains substantially star-shaped or ray-like reference fracture locations 37 which emanate or radiate from the container tip 35, as best seen by referring to FIG. 2.

Figure 3:
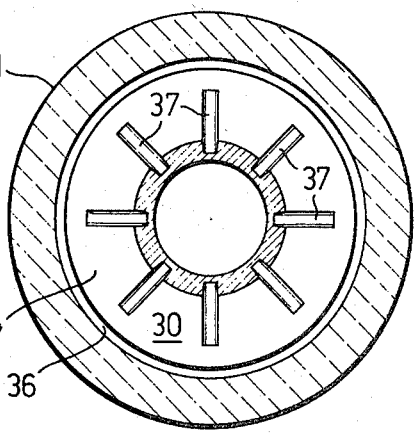
FIG. 3 is a cross-sectional view of the arrangement of FIG. 1, taken substantially along the line III—III thereof.
Figure 4:
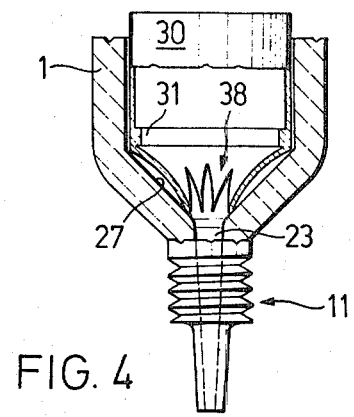
FIG. 4 illustrates partially in sectional view details of the container inserted into the partially illustrated syringe cylinder, and with the container being opened at its end wall.

These reference fracture locations 37 constitute part of the conical end wall 34, the wall thickness of which amounts to approximately one-third of the neighboring wall thickness, reference here being specifically made to FIG. 3. With increased pressure in the container or receptacle 30 the reference fracture locations 37 split open or fracture, whereafter the end wall 34 opens so as to form a substantially crown-shaped opening or orifice 38. FIG. 4 illustrates the container or receptacle 30 after it has been opened at its end or bottom wall 34. There is also clearly evident the manner in which the reinforcement ring member 31 positionally fixes the container or receptacle 30. In this way there is avoided that parts of the container 30 will detach and cause undesired clogging of the equipment.

The container or receptacle 30 is fabricated in conventional manner, for instance by injection molding, is filled with the appropriate liquid and hermetically sealed, for instance by welding.

In the description to follow there will be explained in detail the use of the inventive syringe 9 in conjunction with, strictly by way of example and not limitation, the injection of a contrast agent. Initially a container 30 which is free of air and filled with a physiological saline or salt solution is inserted into the cylinder 1 and the residual volume of the hollow cylinder 1 is filled with a desired quantity of liquid contrast agent. Now there is inserted the piston member 2 into the internal compartment or chamber 1a of the cylinder 1 and contrast agent is ejected therefrom. The container or receptacle 30 which floats in the contrast agent is located, depending upon the position of the cylinder 1, at the neighborhood of the outlet or discharge opening 23 (FIG. 4), or else it is shifted by the action of the piston member 2 towards this outlet or discharge opening 23. Now the liquid contrast agent or medium still contained in the cylinder 1 can flow essentially without any pressure resistance between the cylindrical side wall 32 of the container 30 and the cylinder inner wall 10 towards the outlet or discharge opening 23. The container or receptacle 30 also is not deformed even in the presence of high piston pressures, since the liquid within such container or receptacle 30 is essentially incompressible and the forces acting upon the container 30 mutually compensate one another. After the liquid contrast agent has been ejected out of the cylinder 1, the container or receptacle 30 is then located at the region of the reinforcement ring member 31 upon the substantially cone-shaped or conical inner wall 27 of the cylinder 1, whereas the convex, for instance, domed or cone-shaped configured end face or side 15 of the piston member 2 contacts the rear or top wall 33 of the container 30. Now the piston member 2 is moved further in the direction of the outlet or discharge opening 23, with the result that the pressure within the container or receptacle 30 increases until the reference fracture locations 37 split open or rupture and there is ejected the physiological saline or salt solution. The now slightly compressed together container 30 enables, by further advancing the piston member 2, ejecting essentially all of the liquid flushing agent at the desired velocity.

Both the volumes of the two liquids and also the pressure in the cylinder 1 can be varied within wide limits. With the illustrated exemplary embodiment, which relates to the injection of a contrast agent or medium, the contents of the container or receptacle 30 amounts to about 30 ml, the volume of the liquid contrast agent to about 70 ml, and the pressure in the cylinder 1 between null and 70 bar.

Figure 5:
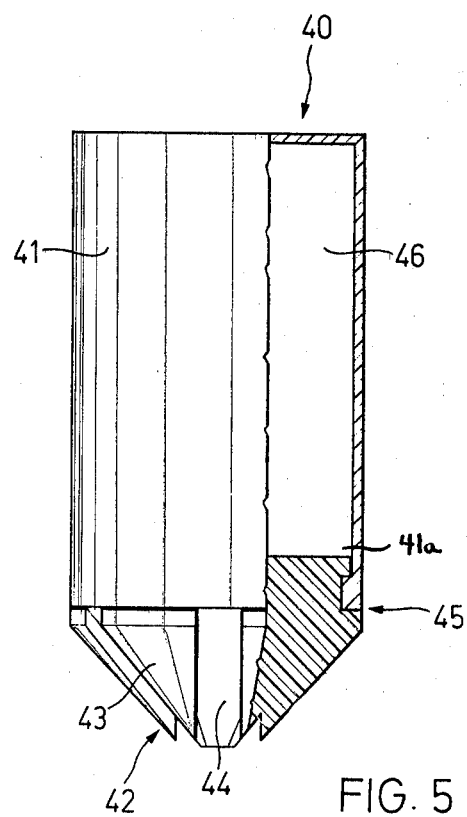
FIG. 5 illustrates partially in sectional view a further construction of container according to the present invention.

FIG. 5 illustrates a further variant construction of the container or receptacle, here generally designated by reference character 40. This container or receptacle 40 comprises an elastic hood member 41, the front opening 41a of which is closed in a fluid tight fashion by a front element or front closure 42, and the internal space or compartment 46 of which is filled with a suitable liquid, here in particular for instance the flushing liquid. The conically tapered front element 42 is preferably provided with cams or detents 43 or equivalent structure, between which there extend grooves or troughs 44 or the like. The hollow hood member 41 is preferably formed of one-piece from silicone rubber or polyethylene, but also could be fabricated from an elastic, cylindrical jacket or shell having a not particularly illustrated closure cover formed of a suitable rigid material.

The emptying of the container 40 is accomplished in the following manner: after ejection of the first liquid the piston member 2 exerts pressure upon the elastic or resilient hood member 41 of the container 40, so that the internal pressure thereof is increased, with the result that the elastic hood member 41 is enlarged and liquid escapes through the reference opening locations 45 between the hood member 41 and the front element 42 and flows into the grooves 44 towards the outlet or discharge opening 23. The container 40 then can be further used in that it again is filled with liquid and the front element or closure 42 is mounted.

It is to be understood that in the context of this disclosure, including the claims, the term "reference fracture means" is intended to be broadly used as encompassing not only one or more reference fracture locations as such but also reference fracture openings or the like or equivalent structure.

While there are shown and described present preferred embodiments of the invention, it is to be distinctly understood that the invention is not limited thereto, but may be otherwise variously embodied and practiced within the scope of the following claims.
ACCORDINGLY,

What we claim is:

1. A syringe for the successive injection of two liquids into the blood vessels of living bodies, comprising:
    a cylinder having opposed ends;

attachment flange means provided at one end of said cylinder;

said other end of said cylinder being provided with an outlet opening for the liquids;

catheter connection means provided at the other end of said cylinder at the neighborhood of said outlet opening;

a piston member insertable into said cylinder;

said cylinder containing an internal compartment;

a container equipped with at least one reference fracture means and provided within the internal compartment of the cylinder between the piston member and the outlet opening;

said container being essentially freely displaceable within the internal compartment of said cylinder in a lenghtwise direction of said cylinder;

said container being filled with one of both liquids and the internal compartment of said cylinder containing the other liquid; and said container, following ejection of the other liquid by said piston member, being opened at said reference fracture means and freeing for injection the liquid contained within said container.

2. The syringe as defined in claim 1, wherein:

said two liquids comprise a contrast agent and a flushing liquid; and said flushing liquid being housed in said container and said contrast agent being located in said internal compartment of said cylinder.

3. The syringe as defined in claim 1, wherein:

said reference fracture comprises a location having a reduced wall thickness and defines a reference fracture location.

4. The syringe as defined in claim 1, wherein:

said piston member possesses an end face of essentially convex configuration.

5. The syringe as defined in claim 1, wherein:

said container contains a substantially cylindrical side wall and a substantially cone-shaped end wall.

6. A syringe for the successive injection of two liquids into the blood vessels of living bodies, comprising:

a cylinder having opposed ends;

attachment flange means provided at one end of said cylinder;

said other end of said cylinder being provided with an outlet opening for the liquids;

catheter connection means provided at the other end of said cylinder at the neighborhood of said outlet opening;

a piston member insertable into said cylinder;

said cylinder containing an internal compartment;

a container equipped with at least one reference fracture means and provided within the internal compartment of the cylinder between the piston member and the outlet opening;

said container being essentially freely displaceable within the internal compartment of said cylinder in a lengthwise direction of said cylinder;

said container being filled with one of both liquids and the internal compartment of said cylinder containing the other liquid;

said container, following ejection of the other liquid by said piston member, being opened at said reference fracture means and freeing for injection the liquid contained with said container;

said container contains a substantially cylindrical side wall and a substantially cone-shaped end wall; and reinforcement means for reinforcing in a substantially ring-shaped configuration said side wall at the region of the end wall of said container.

7. The syringe as defined in claim 1, wherein:

said container contains an end wall provided with the reference fracture means.

8. A syringe for the successive injection of two liquids into the blood vessels of living bodies, comprising:

a cylinder having opposed ends;

attachment flange means provided at one end of said cylinder;

said other end of said cylinder being provided with an outlet opening for the liquids;

catheter connection means provided at the other end of said cylinder at the neighborhood of said outlet opening;

a piston member insertable into said cylinder;

said cylinder containing an internal compartment;

a container equipped with at least one reference fracture means and provided within the internal compartment of the cylinder between the piston member and the outlet opening;

said container being essentially freely displaceable within the internal compartment of said cylinder in a lengthwise direction of said cylinder;

said container being filled with one of both liquids and the internal compartment of said cylinder containing the other liquid;

said container, following ejection of the other liquid by said piston member, being opened at said reference fracture means and freeing for injection the liquid contained with said container;

said container is provided with a plurality of said reference fracture means;

said container possesses an end wall having a tip; and said plurality of reference fracture means are arranged in a substantially star-shaped configuration about the tip of said end wall of said container.

9. A syringe for the successive injection of two liquids into the blood vessels of living bodies, comprising:

a cylinder having opposed ends;

attachment flange means provided at one end of said cylinder;

said other end of said cylinder being provided with an outlet opening for the liquids;

catheter connection means provided at the other end of said cylinder at the neighborhood of said outlet opening;

a piston member insertable into said cylinder;

said cylinder containing an internal compartment;

a container equipped with at least one reference fracture means and provided within the internal compartment of the cylinder between the piston member and the outlet opening;

said container being essentially freely displaceable within the internal compartment of said cylinder in a lengthwise direction of said cylinder;

said container being filled with one of both liquids and the internal compartment of said cylinder containing the other liquid;

said container, following ejection of the other liquid by said piston member, being opened at said reference fracture means and freeing for injection the liquid contained with said container;

said container comprises an elastic hood member having an open front end;

a front element for sealingly closing said open front end of said elastic hood member; and said reference fracture means comprises at least one reference opening location disposed between said hood member and said front element.

10. The syringe as defined in claim 1, wherein:
said syringe is used for the injection of a liquid contrast agent and the subsequent injection of a physiological saline solution.

11. A syringe for the successive injection of two liquids into the blood vessels of living bodies, comprising:
a cylinder having opposed ends;
one of said opposed ends of said cylinder being provided with an outlet opening for the liquids;
a piston member insertable into said cylinder;
said cylinder containing an internal compartment;
a container equipped with at least one reference fracture means and provided within the internal compartment of the cylinder between the piston member and the outlet opening;
said container being essentially freely displaceable within the internal compartment of said cylinder in a lengthwise direction of said cylinder;
said container being filled with one of both liquids and the internal compartment of said cylinder containing the other liquid; and
said container, following ejection of the other liquid by said piston member, being opened at said reference fracture means and freeing for injection the one liquid contained within said container.

12. A syringe for the successive injection of two liquids into the blood vessels of living bodies, comprising:
a cylinder having opposed ends;
one of said opposed ends of said cylinder being provided with a substantially conically-shaped internal wall and an outlet opening for the liquids;
said cylinder receiving a first one of said two liquids;
a piston member insertable into said cylinder;
a container placed in said cylinder between the piston member and the outlet opening;
said container being essentially freely displaceable within said cylinder in a lengthwise direction of said cylinder;
said container defining a side facing said conically-shaped internal wall of said cylinder and being equipped on said side with a correspondingly substantially cone-shaped end wall provided with at least one reference fracture means;
said container being filled with a second one of said two liquids; and
said container, following ejection of said first liquid by said piston member, being automatically opened at said at least one reference fracture means due to the cooperation of said conically-shaped internal wall of said cylinder and said cone-shaped end wall of said container and freeing for injection said second liquid contained within said container.

13. The syringe as defined in claim 12, further including:
attachment flange means provided at the other one of said two opposed ends of said cylinder.

14. The syringe as defined in claim 12, wherein:
said container comprises a substantially cylindrical hood member made of elastic material;
said end wall of said container being formed by a substantially cone-shaped front element which sealingly closes said hood member and defines a transitional region therebetween;
said at least one reference fracture means forming a predetermined number of reference fracture locations arranged in said transitional region;
said front element defining an outer surface facing said conically-shaped internal wall of said cylinder; and
said outer surface including radially extending grooves.

15. The syringe as defined in claim 12, wherein:
said container defines a substantially cylindrical side wall and a transitional region between said side wall and said end wall; and
said transitional region comprising an annular reinforcement.

16. The syringe as defined in claim 12, wherein:
said container defines a substantially cylindrical portion;
said end wall defining a tip portion;
said at least one reference fracture means comprising a predetermined number of reference fracture locations having a reduced wall-thickness; and
said reference fracture locations radially extending from said tip portion to said cylindrical portion.

17. The syringe as defined in claim 12, further including:
catheter connection means provided at said one end of said cylinder.

* * * * *